(12) United States Patent
McCormick et al.

(10) Patent No.: US 7,666,671 B2
(45) Date of Patent: Feb. 23, 2010

(54) METHODS FOR FIXING CYTOLOGICAL SAMPLES

(75) Inventors: Patrick J. McCormick, Rutland, MA (US); Kevin Patenaude, Lowell, MA (US); Robert Sakal, Bolton, MA (US)

(73) Assignee: CYTYC Corporation, Marlborough, MA (US)

( * ) Notice: Subject to any disclaimer, the term of this patent is extended or adjusted under 35 U.S.C. 154(b) by 407 days.

(21) Appl. No.: 11/538,905

(22) Filed: Oct. 5, 2006

(65) Prior Publication Data

US 2007/0105187 A1    May 10, 2007

Related U.S. Application Data

(60) Provisional application No. 60/724,886, filed on Oct. 11, 2005.

(51) Int. Cl.
 C12N 5/00     (2006.01)
 G01N 1/30     (2006.01)
 G01N 33/48    (2006.01)

(52) U.S. Cl. ..................... 435/325; 435/4; 435/40.5

(58) Field of Classification Search .............. None
 See application file for complete search history.

(56) References Cited

U.S. PATENT DOCUMENTS

| 4,120,991 A | 10/1978 | Ornstein et al. |
| 4,395,493 A | 7/1983  | Zahniser et al. |
| 2002/0009767 A1 | 1/2002 | Muraca |
| 2003/0054342 A1 | 3/2003 | Star |
| 2003/0207456 A1 * | 11/2003 | Ostgaard et al. ............... 436/43 |
| 2007/0134798 A1 * | 6/2007 | McCormick et al. .......... 436/18 |

FOREIGN PATENT DOCUMENTS

| JP | 05281109 A | * 10/1993 |
| WO | 9304193 | 3/1993 |
| WO | 0167067 | 9/2001 |
| WO | 2006076432 | 7/2006 |

OTHER PUBLICATIONS

Sabine Eisenberger, Godehard Hoppe, Walter Pyerin, Karin Ackermann, "High-quality RNA preparation for transcript profiling of osteocytes from native human bone microdissections" Analytical Biochemistry, Academic Press, New York, NY, vol. 335, No. 2, Dec. 2004, pp. 260-266.
PCT International Search Report for PCT/US2006/039003, Applicant CYTYC Corporation, Forms PCT/ISA/210 and 220, dated Apr. 18, 2007 (4 pages).
PCT Written Opinion of the International Search Authority for PCT/US2006/039003, Applicant: CYTYC Corporation, Form PCT/ISA/237, dated Apr. 18, 2007 (7 pages).

* cited by examiner

*Primary Examiner*—Christopher R Tate
*Assistant Examiner*—Aaron J Kosar
(74) *Attorney, Agent, or Firm*—Vista IP Law Group LLP

(57) ABSTRACT

A method of fixing a biological sample on a slide for cytological analysis, includes transferring a sample to a slide, applying a material having a slide-fixing amount of an inactivated, fixative to the slide, and activating the fixative. By way of example, the material may comprise a tape impregnated with the inactivated fixative, which tape may be removed from the slide after the fixative is activated.

17 Claims, 4 Drawing Sheets

METHODS FOR FIXING CYTOLOGICAL SAMPLES

RELATED APPLICATION DATA

The present application claims the benefit under 35 USC §119 of provisional application Ser. No. 60/724,886, filed Oct. 11, 2005. The aforementioned application is hereby incorporated by reference herein in its entirety.

FIELD OF INVENTION

The present invention relates to the preparation of cytological samples. Specifically, the invention relates to methods, manual and automated, for fixing samples for cytological analysis. The invention also relates to materials used to fix a sample for cytological analysis.

DESCRIPTION OF RELATED ART

Cytology is the branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "Pap smear" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions are typically applied to the cells on the glass slide, often called a cell "smear," for facilitating examination and for preserving the specimen for archival purposes.

Prior techniques for fixing samples utilized liquid fixative solutions that were sprayed onto the slides and then allowed to dry. For example, in automated systems, a glass slide containing the cells to be analyzed is positioned such that the slide receives one or more doses of fixative solution. Often, the fixative solution is delivered from a nozzle, often pressurized, and often the fixative solution is allowed to air-dry between doses.

Drawbacks to liquid fixative solutions used in this manner included build-up of excess solution on surrounding areas, e.g., neighboring slides and instrumentation. This occurs because the delivery from the nozzle to the slide is imprecise. Eliminating the fixative from curing onto the instrumentation will lengthen instrument operating time and reduce the need for service and maintenance due primarily to improper cleaning techniques with the instrument.

SUMMARY OF THE INVENTION

In one embodiment, a method of fixing a biological sample on a slide for cytological analysis, includes transferring a sample to a slide, applying a material having a slide-fixing amount of an inactivated, fixative to the slide, and activating the fixative. By way of example, the material may comprise a tape impregnated with the inactivated fixative, which tape may be removed from the slide after the fixative is activated.

Other and further embodiments and aspects of the invention will become apparent upon review of the following detailed description.

DETAILED DESCRIPTION OF ILLUSTRATED EMBODIMENTS

Figure 1A:
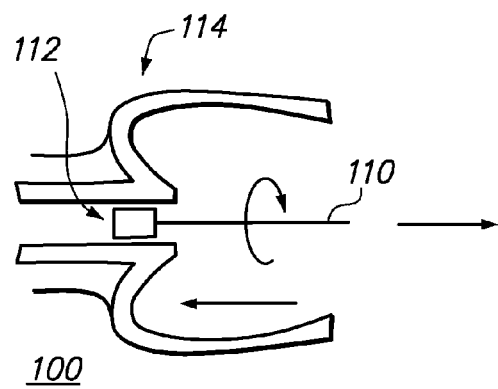
FIG. 1 is a schematic illustration of a typical manual sample fixing procedure.
Figure 1B:
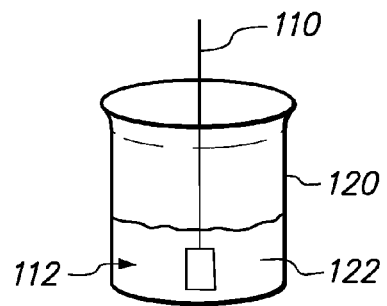
Figure 1C:
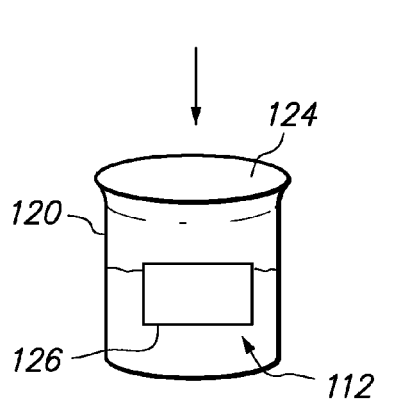
Figure 1D:
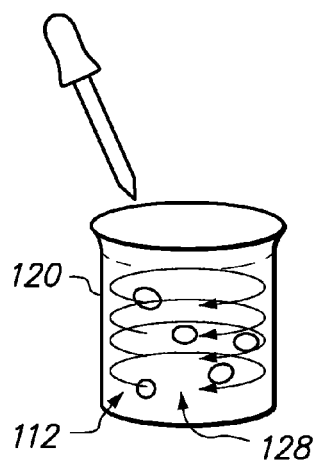
Figure 1E:
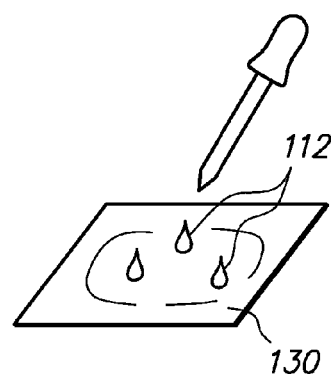
Figure 1F:
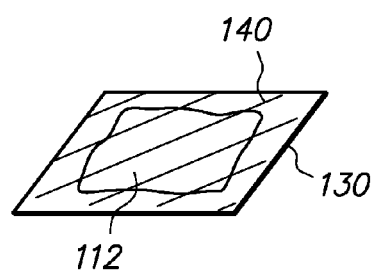
Figure 1G:
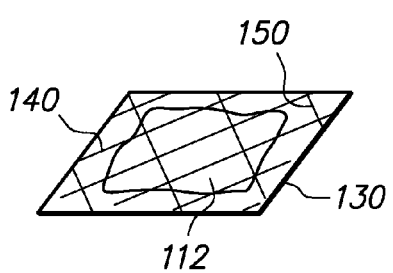

As used herein, a "cytological sample" is defined as any specimen from an organism, preferably a mammal, in sufficient amount to be characterized and/or analyzed. A cytological sample, by way of non-limited example, includes cell samples, skin samples, tissue samples, and mucosal samples.

As used herein, the phrase, "characterizing and/or analyzing" a cytological sample refers to studying the sample with the assistance of something more than the unassisted human eye, e.g., using the assistance of a microscope having a magnifying lens objective.

As used herein, the term "fixative" means a composition, which may or may not be in liquid form that fixes the cytological sample such that the cytological sample is adhered to the slide for a period of time sufficient to characterize and/or analyze the cytological sample.

As used herein, an "inactivated fixative" refers to fixative that requires activation, such as due to exposure to light, heat, or chemical treatment, prior to use.

As used herein, a "fixative tape" means a tape or tape-like substance having an active ingredient that is a fixative.

As used herein, a "fixative-containing material" is a material which has been permeated and/or impregnated with inactivated fixative such that upon contact with water, staining solution, and/or another specified component, the fixative is released from the material.

FIG. 1 depicts an example of a typical manual sample fixing procedure 100. In FIG. 1A, a broom-like device 110 is used to obtain a cytological sample 112 from a patient 114. In FIG. 1B, the broom-like device 110 is rinsed in a sample preserving solution 122 contained within a vial 120, releasing the cytological sample 112. Next, in FIG. 1C, the vial 120 is capped 124 and labeled 126. Next, in FIG. 1D, the sample vial 120 is rotated 230, dispersing debris and mucus while thoroughly mixing the cell sample 112. In FIG. 1E, sample cells 112 are transferred onto a glass slide 130. FIG. 1F, next, depicts that a fixative solution 140 has also been placed on the glass slide 130, on top of the sample 112, and allowed to dry. Finally, FIG. 1G depicts a staining solution 150 that has been applied to the fixed sample 112.

Figure 2A:
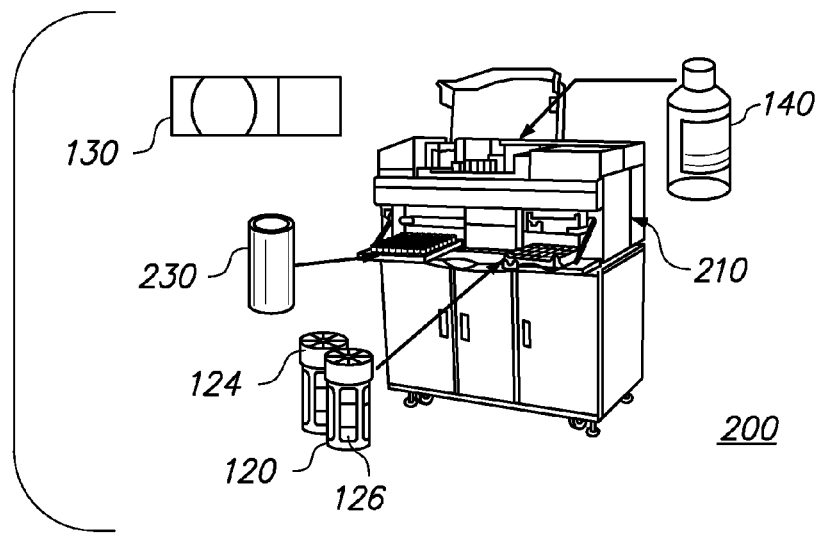
FIG. 2 is a schematic illustration of a typical automated sample fixing procedure.
Figure 2B:
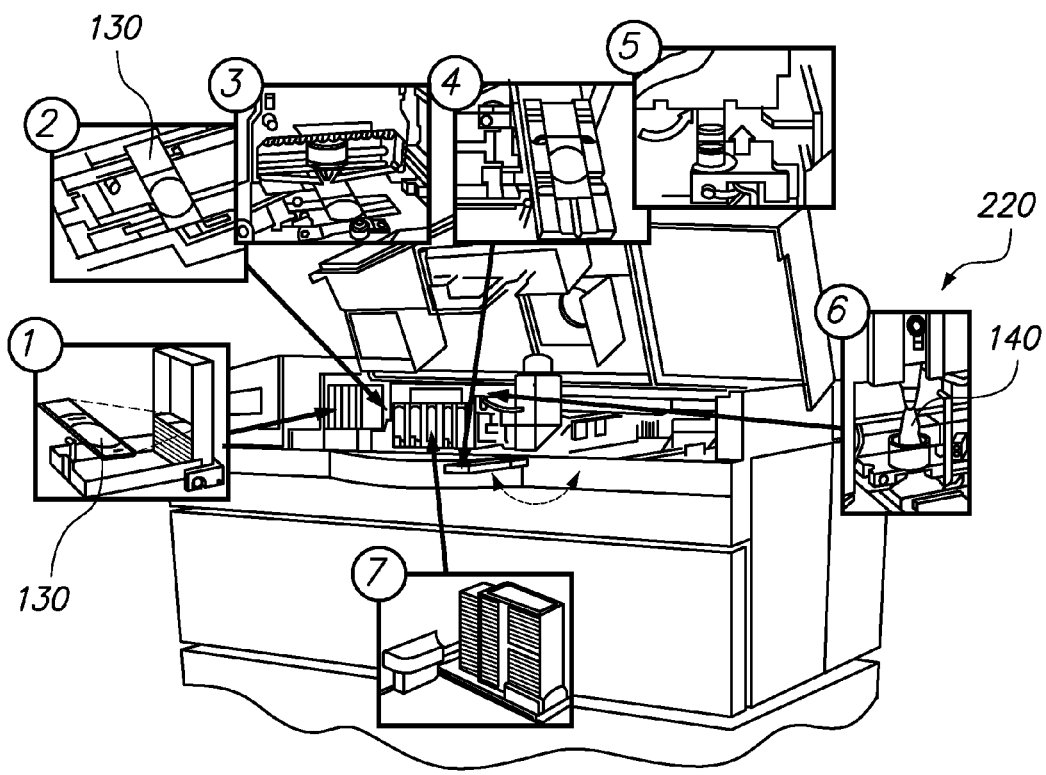

FIG. 2 depicts an example of a typical automated sample fixing procedure 200. The automated procedure 200 is the same as the manual procedure 100 (see FIG. 1 and its description, above) through the capping 124 and labeling 126 step (1C). However, in the automated procedure 200 the processor 210 then carries out the remaining steps (1D-G). Notably, FIG. 2B (6) depicts a fixative dispenser 220, which dispenses fixative solution 140 two times, separated by, for example, a period of approximately ten seconds.

Figure 3A:
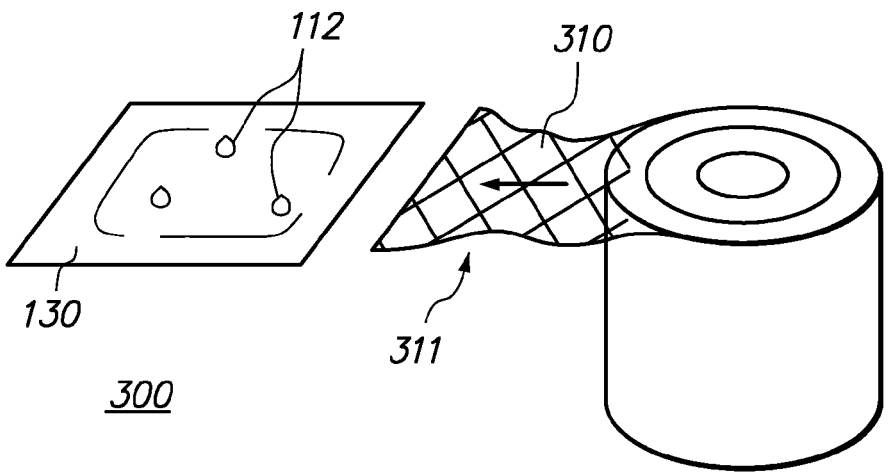
FIG. 3 is a schematic illustration of a manual sample fixing procedure using the fixative tape described herein.
Figure 3B:
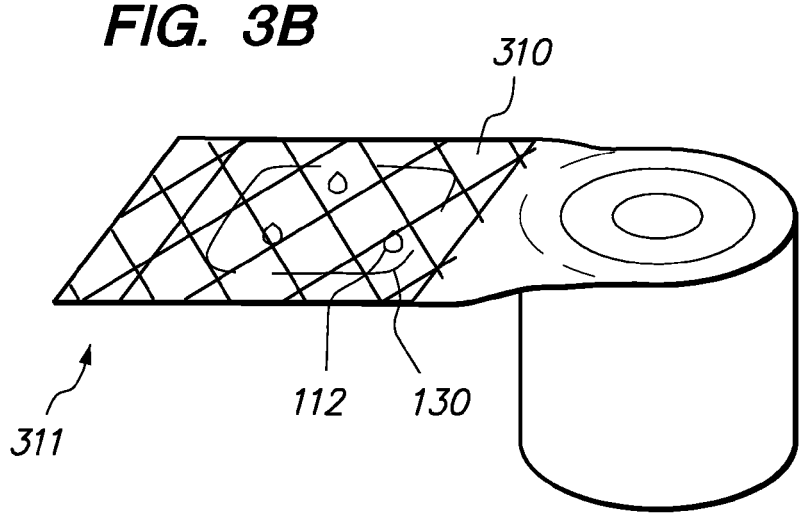
Figure 3C:
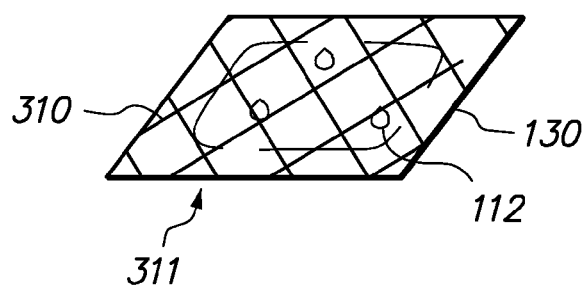
Figure 4A:
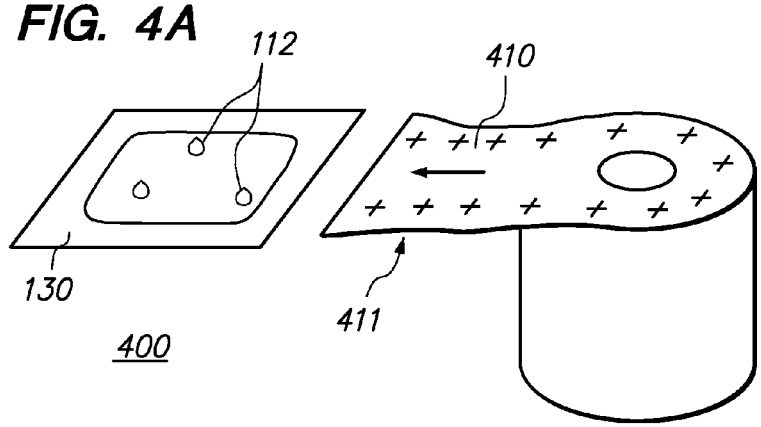
FIG. 4 is a schematic illustration of a manual sample fixing procedure using the fixative-containing material described herein.
Figure 4B:
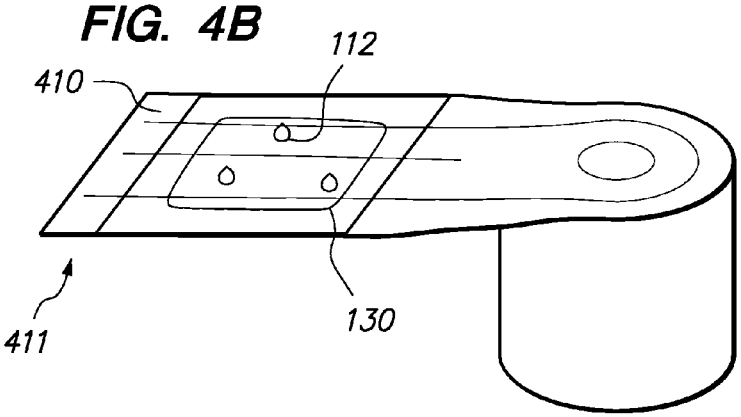
Figure 4C:
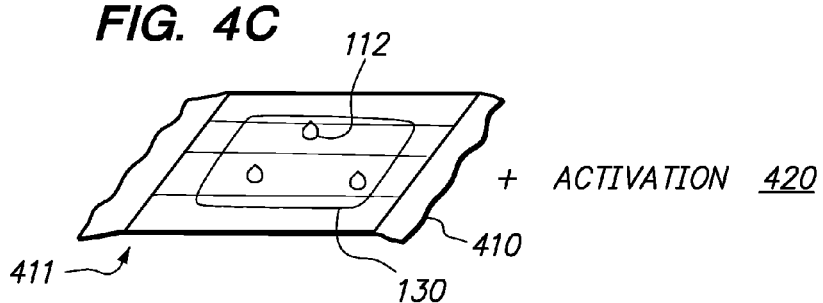
Figure 4D:
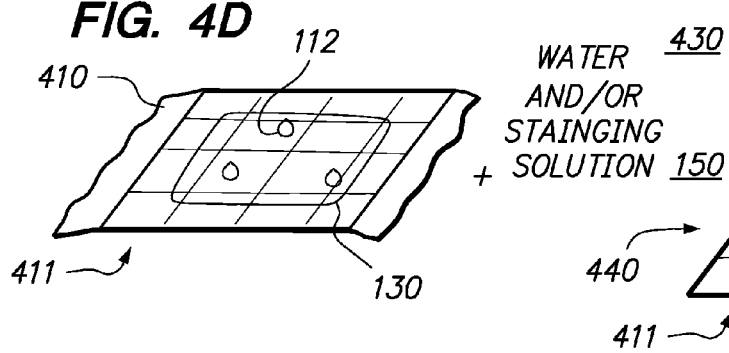
Figure 4E:
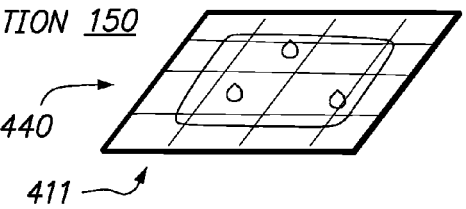

FIG. 3 depicts a manual sample fixing procedure 300 using a fixative tape described herein. In FIG. 3A, a glass slide 130 is shown which contains a cytological sample 112. In FIG. 3B, an inactivated tape 310 having a fixative 311 has been strewn across the top of the glass slide 130 containing the cytological sample 112. FIG. 3C depicts the glass slide 130 containing the cytological sample 112 and inactivated fixative tape 310, awaiting activation prior to characterization and/or analysis.

FIG. 4 depicts a manual sample fixing procedure 400 using a fixative-containing material 410 described herein. The material 410 includes a fixative 411. In FIG. 4A, a glass slide 130 is shown which contains a cytological sample 112. In FIG. 4B, an inactivated fixative-containing material 410 has been strewn across the glass slide 130 containing the cytological sample 112. In FIG. 4C, the inactivated fixative-containing material 410 rests atop the glass slide 130 containing the cytological sample 112, awaiting activation. Following activation 420, see FIG. 4D, water 430 and/or staining solution 150 is applied to the slide 130. The water 430 and/or staining solution 150 dissolve the material 410, leaving the fixed, stained, cytological sample 440, see FIG. 4E, ready for characterization and/or analysis.

One embodiment features a method for fixing a sample 112, comprising transferring a sample 112 to a slide 130, applying a slide-fixing amount of an inactivated fixative, and activating said fixative.

Another embodiment features a method for fixing a sample 112, comprising transferring a sample 112 to a slide 130, applying a fixing amount of an inactivated fixative-containing material, activating said fixative, and removing said material.

Yet another embodiment features a sample-fixing material, comprising inactivated fixative and permeable tape, e.g. a permeable tape 310.

Yet another embodiment features a kit for fixing a cell sample 112, comprising one or more slides 130 and inactivated fixative and/or inactivated fixative-containing material, e.g., material 410.

When the fixative is in the form of a tape 310, the tape 310 is positioned such that it contacts the sample 112 positioned on the slide 130. Upon activation, the fixative 311 from the tape 130 adheres the cytological sample 112 to the slide 130 for a period of time sufficient to characterize and/or analyze the cytological sample 112.

When the fixative is in the form of a fixative-containing material 410, the material 410 is positioned such that it contacts the sample 112 positioned on the slide 130. Upon activation, the fixative 411 from the fixative-containing material 410 adheres the cytological sample 112 to the slide 130 for a period of time sufficient to characterize and/or analyze the cytological sample 112. Following activation, the material 410 is exposed to a substance, such as water 430 and/or slide-staining solution 150, which removes the material 410 yet leaves the activated fixative 411 in place. Alternatively, the material 410 may be physically removed, leaving the activated fixative 411 in place.

According to one embodiment, an inactivated fixative may be activated due to heat treatment, light treatment, and/or chemical treatment. Preferred activation occurs via exposure to ultra-violet light. For example, ultra-violet activation can occur due to the use of a hand-held LED light source, such as the Loctite 7700 Hand Held LED Light Source (available from Loctite).

According to one embodiment, the fixative is typically employed in the range of from about 0.01 mL to about 50 mL per slide 130. Preferably, from about 1 mL to about 25 mL is applied to each slide 130. More preferably, from about 10 mL to about 25 mL is applied to each slide 130. Even more preferably, about 20 mL is applied to each slide 130.

In order to further illustrate the present invention and the advantages thereof, the following examples are given, it being understood that the same are intended only as illustrative and in nowise limitative. Various components described in the following examples are shown in FIG. 2.

EXAMPLE 1

In one embodiment of the invention, a system includes a first loading station for receiving a plurality of samples, such as a sample vial tray with a plurality of closed, capped sample vials 120. The vials 120 include particles of interest, such as cells, tissue samples, assay product, or other material, typically dispersed in a fluid medium. A sample transfer assembly, such as a sample vial transfer assembly, serially retrieves each sample vial 120, unscrewing a cap 124 thereof, and positioning the now open vial 120 in a position for cooperation with a sample collector and filter 230, which may be drawn automatically from another tray having a plurality of sample collectors. A sample collector or other mechanism prepares the sample 112 for collection such as, for example, by agitating the sample 112 in a manner so as to create a generally uniform dispersion of particles of interest throughout the sample 112. Once the particles cells 112 are dispersed, collected against the filter 230, and transferred to a slide 130 drawn automatically from a slide dispenser having a plurality of clean slides stored therein, the slide 130 is then contacted with inactivated fixative, e.g., fixative 311 or 411, from a fixative containing material, e.g., material 310 or 410). For example, the fixative can be carried by a tape and can be housed on a spool. Next, the fixative (is activated. The slide 130 may then be transferred to one of a number of multi-position staining racks previously loaded in the system. Once a first patient's specimen is prepared, the open sample vial 120 is recapped and replaced in the sample vial tray. The filter 230 of the sample collector may be breached to prevent reuse and resultant inter-sample contamination. The next sample vial 120 can then be retrieved and the specimen preparation method repeated until all of the sample vials 120 are processed. Accordingly, once the system operator loads the sample vial tray, sample collector tray, slide dispenser, and staining racks, and initiates the automatic sequence, the system can operate unattended.

EXAMPLE 2

In another embodiment of the invention, a system includes a first loading station for receiving a plurality of samples, such as a sample vial tray with a plurality of closed, capped sample vials 120. The vials 120 include particles of interest, such as cells, tissue samples, assay product, or other material, typically dispersed in a fluid medium. A sample transfer assembly, such as a sample vial transfer assembly, serially retrieves each sample vial 120, unscrewing a cap 124 thereof, and positioning the now open vial 120 in a position for cooperation with a sample collector and filter 230, which may be drawn automatically from another tray having a plurality of sample collectors. A sample collector or other mechanism prepares the sample 112 for collection such as, for example, by agitating the sample in a manner so as to create a generally uniform dispersion of particles of interest throughout the sample 112. Once the particles cells 112 are dispersed, collected against the filter 230, and transferred to a slide 130 drawn automatically from a slide dispenser having a plurality of clean slides stored therein, the slide 130 is then contacted with inactivated fixative-containing material, such as material 310 or 410, which can be housed on a spool. Next, the fixative, e.g., 311 or 411, is activated. The slide 130 may then be transferred to one of a number of multi-position staining racks previously loaded in the system. While in the staining rack, the staining solution 150 is exposed to the slide 130, thereby removing the material 310 or 410. The material is transferred with the excess staining solution 150 to a waste receptacle.

Once a first patient's specimen is prepared, the open sample vial 120 is recapped and replaced in the sample vial tray. The filter 230 of the sample collector may be breached to prevent reuse and resultant inter-sample contamination. The next sample vial 120 can then be retrieved and the specimen preparation method repeated until all of the sample vials 120 are processed. Accordingly, once the system operator loads the sample vial tray, sample collector tray, slide dispenser, and staining racks, and initiates the automatic sequence, the system can operate unattended.

The forgoing illustrated and described embodiments and examples of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims.

What is claimed is:

1. A method of fixing a biological sample to a slide, comprising:
   (a) transferring a biological sample to a slide;
   (b) applying a fixative carrier material to the biological sample and slide obtained from step (a), the fixative carrier material comprising a slide-fixing amount of an inactivated fixative;
   (c) activating said inactivated fixative; and,
   (d) removing the fixative carrier material from the slide while retaining the activated fixative on the slide.

2. The method of claim 1, wherein the amount of the inactivated fixative is between 0.01 mL and 50 mL.

3. The method of claim 2, wherein the amount of the inactivated fixative is about 20 mL.

4. The method of claim 1, wherein said activating comprises applying heat to the slide obtained from step (b).

5. The method of claim 1, wherein said activating comprises applying a chemical activator of said inactivated fixative to the slide obtained from step (b).

6. The method of claim 1, wherein said activating comprises applying light to the slide obtained from step (b).

7. The method of claim 6, wherein said applying light comprises exposing the slide from step (b) to ultra-violet light.

8. The method of claim 1, wherein said fixative carrier material comprises a tape impregnated with the inactivated fixative.

9. The method of claim 1, wherein removing said fixative carrier material comprises removing said fixative carrier material with water.

10. The method of claim 1, wherein removing said fixative carrier material comprises removing said fixative carrier material with a slide-staining solution.

11. The method of claim 1, wherein removing said fixative carrier material comprises removing said fixative carrier material with both water and a slide-staining solution.

12. The method of claim 1, wherein removing said fixative carrier material comprises physically removing said fixative carrier material.

13. A method of fixing a biological sample, comprising:
   (a) transferring a biological sample to a slide;
   (b) applying a fixative carrier material to the biological sample and slide obtained from step (a), the fixative carrier material comprising a slide-fixing amount of an inactivated fixative;
   (c) activating said inactivated fixative by applying heat to the slide, exposing the slide to light treatment, or treating the slide with a chemical; and,
   (d) removing the fixative carrier material from the slide while retaining the activated fixative on the slide.

14. The method of claim 13, wherein said exposing the slide to light comprises exposing the slide from step (b) to ultra-violet light.

15. The method of claim 13, wherein said fixative carrier material comprises a tape impregnated with the inactivated fixative.

16. A method of fixing a biological sample, comprising:
   (a) transferring a biological sample to a slide;
   (b) applying a tape to the biological sample and slide obtained from step (a), said tape being impregnated with a slide-fixing amount of an inactivated fixative;
   (c) activating said inactivated fixative by applying heat to the slide, exposing the slide to light, or treating the slide with a chemical; and,
   (d) removing said tape from the slide such that the activated fixative is retained on the slide after removing said tape.

17. The method of claim 16, wherein said activating comprises exposing the slide to ultra-violet light.

* * * * *

UNITED STATES PATENT AND TRADEMARK OFFICE
CERTIFICATE OF CORRECTION

PATENT NO. : 7,666,671 B2  Page 1 of 1
APPLICATION NO. : 11/538905
DATED : February 23, 2010
INVENTOR(S) : McCormick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Seventh Day of December, 2010

David J. Kappos
*Director of the United States Patent and Trademark Office*